US005648546A

United States Patent [19]

Bergfeld et al.

[11] Patent Number: 5,648,546

[45] Date of Patent: Jul. 15, 1997

[54] METHOD FOR MANUFACTURING TERT-BUTYLAMINE

[75] Inventors: Manfred Bergfeld, Erlenbach-Mechenhard; Martin Nywlt, Obernburg, both of Germany

[73] Assignee: Akzo Nobel, N.V., Velpergwg, Netherlands

[21] Appl. No.: 555,018

[22] Filed: Nov. 13, 1995

Related U.S. Application Data

[63] Continuation-in-part of Ser. No. 295,877, Sep. 6, 1994, abandoned, which is a continuation of PCT/EP93/00482, Mar. 3, 1993.

[30] Foreign Application Priority Data

Mar. 5, 1992 [DE] Germany .......................... 42 06 992.0

[51] Int. Cl.$^6$ .................................................. C07C 209/60

[52] U.S. Cl. ............................................................. 564/485

[58] Field of Search .............................. 564/485; 502/66, 502/79, 77

[56] References Cited

U.S. PATENT DOCUMENTS

| | | | |
|---|---|---|---|
| 3,937,791 | 2/1976 | Garwood et al. | 208/120 |
| 4,093,560 | 6/1978 | Kerr et al. | 208/120 |
| 4,465,884 | 8/1984 | Degnan et al. | 585/415 |
| 4,929,758 | 5/1990 | Taglieber et al. | 564/485 |
| 5,107,027 | 4/1992 | Knifton et al. | 564/485 |
| 5,304,681 | 4/1994 | Knifton et al. | 564/485 |

FOREIGN PATENT DOCUMENTS

| | | |
|---|---|---|
| 0 039 918 | 11/1981 | European Pat. Off. . |
| 0 305 564 | 3/1989 | European Pat. Off. . |
| 3 326 579 A1 | 1/1985 | Germany . |
| 3 940 349 A1 | 6/1991 | Germany . |

OTHER PUBLICATIONS

Breck et al., "Zeolite Chemistry II. The Role of Aluminum in the Hydrothermal Treatment of Ammonium–Exchanged Zeolite Y, Stabilization," in *Molecular Sieves–II,* Katzer, Ed., American Chemical Society: Washington, DC (1977).

"Heterogeneous Acid–Catalyzed Amination of Isubutene to tert–Butylamine", Journal of Organic Chemistry, Bd. 53. Nr. 19, Sep. 16, 1988, Washington US, pp. 4594–4596.

"Direct Amination of 2–Methylpropene with Amonia Into t–Butylamine on Proton–Exchanged ZSM–5 Zeolite Catalyst", Chemistry Letters, Nov. 6, 1991, Tokyo JP., M. Tabata et al., pp. 1027–1028.

*Primary Examiner*—Brian M. Burn
*Attorney, Agent, or Firm*—Oliff & Berridge

[57] ABSTRACT

The invention relates to a method for manufacturing tert-butylamine from isobutene and ammonia in the presence of a silica alumina catalyst. The catalyst is in acid form, has an Si/Al ratio that has been adjusted by steam dealumination, has a crystallinity of at least 95%, and has an $Na_2O$ content of less than 0.2 wt. %. The reaction is preferably conducted in the gas phase, with unreacted ammonia and unreacted isobutene being recycled into the reaction process. The selectivity of the catalyst for the formation of tert-butylamine is at least 99.5%.

15 Claims, 2 Drawing Sheets

METHOD FOR MANUFACTURING TERT-BUTYLAMINE

This is a Continuation-in-Part of application Ser. No. 08/295,877, filed Sep. 6, 1994, (now abandoned) which in turn is a national stage application of PCT/EP93/00482, filed Mar. 3, 1993.

FIELD OF THE INVENTION

The invention relates to a method for manufacturing tert-butylamine from ammonia and isobutene.

BACKGROUND

Industrially, tert-butylamine is a very important intermediate for making dyes, pesticides, and rubber additives.

The industrial processes are based on the so-called Ritter reaction in which, by addition of hydrocyanic acid and water to olefins or by the substitution reaction of alcohols with hydrocyanic acid and water, a formamide derivative is first formed, hydrolysis of which leads to the desired amine. Sulfuric acid is added in nearly equimolar quantities as a catalyst. Formic acid is produced as a by-product. The process involves toxic and aggressive substances, the handling, separation, and reprocessing of which are technologically and financially intensive.

The addition of ammonia to isobutene on which the present invention is based is an equilibrium reaction and has been investigated for a very long time without leading to an industrial process. Because of the position of the equilibrium, only very low conversions, less than 20%, are achieved under industrial reaction conditions. Economic recycling of the unreacted educt is achievable only with very high selectivity for tert-butylamine. A method based on the addition reaction therefore has to be characterized by high product selectivity, long catalyst life, and high catalyst activity.

A number of attempts have been made in the past to develop an industrially usable process from the addition reaction, but thus far it has proved impossible to develop such a process that meets all the requirements described briefly below.

An industrially usable process is characterized above all by minimizing the ratio between recycling streams and product streams. This means using equimolar amounts of ammonia and isobutene. It is important, however, for this step taken to optimize the recycling ratio not to diminish the selectivity of the catalyst for tert-butylamine.

Such an industrially usable process must however also be able to tolerate variations in concentration, namely a deficiency of ammonia should not increase formation of by-products (oligomerization and cracking of isobutenes, and formation of di(tert-butyl)amines).

In the previously known processes for manufacturing tert-butylamine, however, the ammonia:isobutene ratio was 1.5:1 or more.

Two contradictory demands are made in the first instance on the catalyst candidate for the reaction: The catalyst should have high activity to come as close as possible to the equilibrium conversion, but it should not promote by-product formation and coking (high selectivity).

Also, the catalyst should be sufficiently reactive at temperatures below approximately 320° C., as otherwise the reactants and reaction products would be thermally decomposed and increased coking or by-product formation would occur.

In a recycling process usable on an industrial scale, suppression of by-products such as highly volatile amines (methylamine) is very important since these could otherwise be fed back into the reaction as low boilers and could there react to form mixed amines (such as tert-butylmethylamine). After several cycles, the proportion of these by-products would increase continuously so that the yield of tert-butylamine would be inadequate and the cost of producing pure (greater than 99.5%) tertbutylamine would be increased dramatically by expensive separation operations.

Thus, it must be possible to operate an industrial process with technical raw materials without costly pretreatment. In general, such raw materials also have certain proportions of impurities which of course are expected to be inert in the recycle loop and have no negative effect on the activity/selectivity and life of the catalyst, and can easily be separated.

In particular, n-butene, which is normally present in technical isobutene (educt) in small quantities, should not be reacted with ammonia to form isobutylamine, as otherwise the product specifications (highly pure (>99.5%) tert-butylamine) are not met. In this case as well, the recycling process described (e.g. TBA/isobutylene separation) would be heavily burdened by expensive separation stages.

In principle, synthesis of tert-butylamine from ammonia and isobutene is known for example from EP-A 0 039 918 where good selectivities can be achieved with comparatively low conversion, but where selectivity declines as conversion increases. Because of their fast coking, the catalysts used in this process have only short lives.

If, as may be gathered from DE-OS 33 26 579, the prior-art catalyst is selected for long life, i.e. a low degree of coking, tert-butylamine selectivities of less than 98.7% are achieved. The gallium silicate zeolite referred to in DE-OS 39 40 349 also has selectivity of only approximately 98%; in this case, however, very high pressures are required for quantitative conversion.

In a number of other prior-art processes as well, because of the stoichiometric equilibrium, by-products arise in the classical substitution reaction which have to be removed in expensive purification steps.

A goal of the invention is to provide a method with which tert-butylamine can be manufactured in a simple and environmentally benign manner, and in which no by-products that would have to be expensively removed from the reaction mixture are produced. In addition, the catalyst should have a long operating life as well as high selectivity and activity.

SUMMARY OF THE INVENTION

Goals of this invention are achieved by a process for producing tert-butylamine by reacting isobutene and ammonia on a special silica alumina catalyst under highly specific conditions so that the purity of the tert-butylamine produced is at least 99.5% and can be used (further processed) after separation (recycling) of the (low-boiling) educts directly without fractional distillation.

DETAILED DESCRIPTION OF PREFERRED EMBODIMENTS

Figure 1:
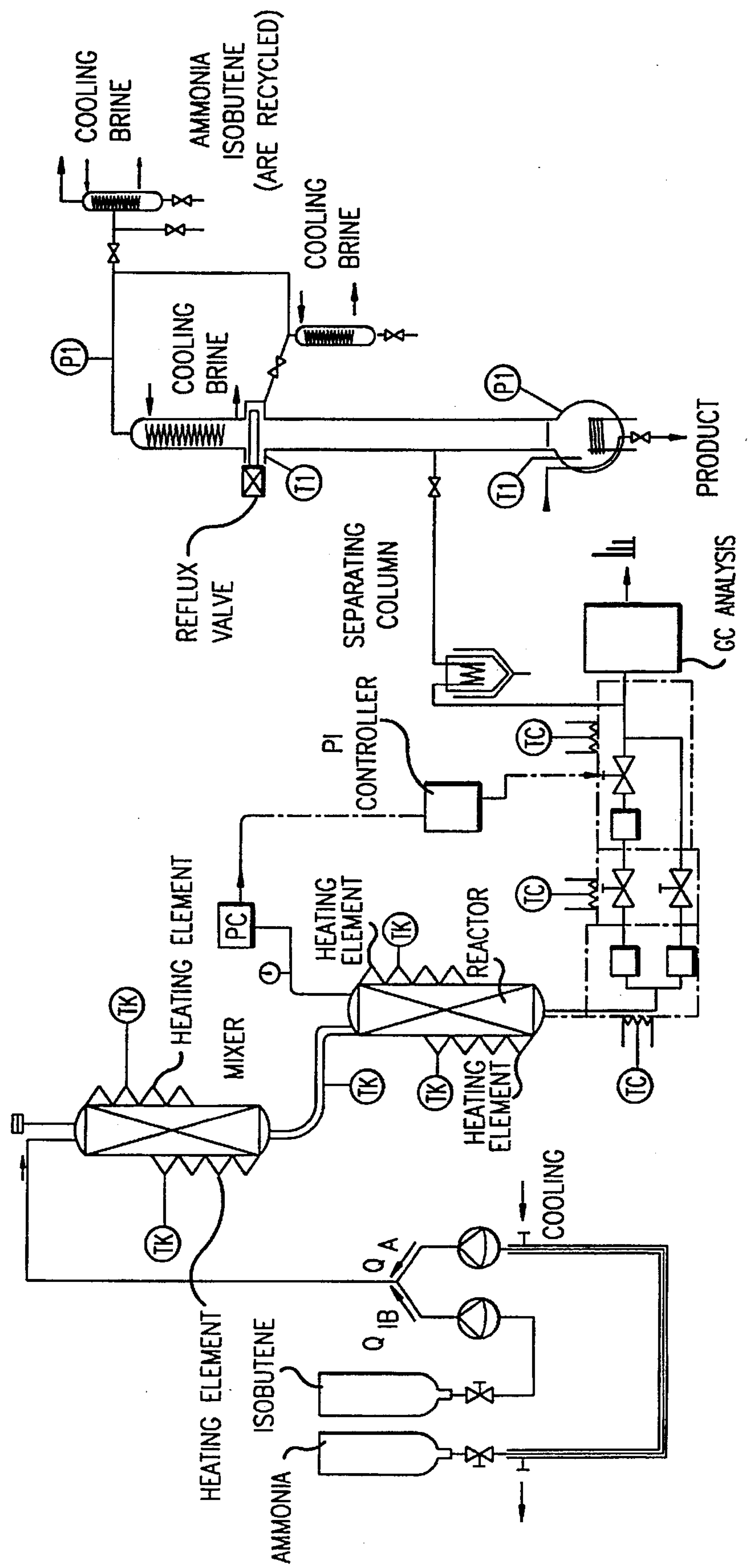
FIG. 1 is a schematic diagram of the process of the invention.

When a technical isobutene (purity<99.5%) is used, the purity of the tert-butylamine formed is shown by gas chromatography to be >99.5%. When a pure isobutene is used (purity>99.9%), the purity of the tert-butylamine formed after gas chromatography is more than 99.8%.

The purity is determined by the usual gas chromatography methods (oven temperature: 80° C.; carrier gas $N_2$; FID detector; sample loop: 12.5 μl; column 30 m).

It is preferable to conduct the reaction in a tubular reactor. In another embodiment, the reaction is conducted in an adiabatic packed bed reactor.

The material of the reactor is preferably inert to the reactants. In one embodiment of the invention, the reactor is made of a Cr-Ni steel. In another embodiment, the reactor is made of a nickel-based material of the Inconel 600 type.

It is preferable to conduct the reaction at temperatures of 200° to 350° C. It is particularly preferable to conduct the reaction at temperatures of 270° to 320° C.

It is preferable to conduct the reaction at pressures of to 50 to 350 bars. It is particularly preferable to conduct the reaction at pressures of 50 to 200 bars.

Catalyst loading with the educts is more than 2 mol/(kg cat.h). Catalyst loading of 5 to 60 mol/(kg cat.h) is preferred. Catalyst loading of 10 to 30 mol/(kg cat.h) is particularly preferred.

The reactor is started by taking the following steps:

a) multiple flushing with $N_2$ until the air has been completely removed, b) heating to operating temperature, c) flushing with ammonia, d) setting operating pressure under an ammonia atmosphere, e) adding isobutene to the reactor up to the desired molar ratio, f) after steady-state reaction equilibrium is reached, adding the educts in the desired molar ratio and continuously discharging the reaction mixture at a corresponding rate.

The molar ratio of ammonia to isobutene is 0.3:1 to 10:1. It is preferable for the molar ratio of ammonia to isobutene to be 0.9:1 to 4:1.

The method is further characterized by the selectivity of the catalyst being>99.8% even with $NH_3$:isobutene molar ratios of less than 1:1.

In one embodiment of the invention, the catalyst is a zeolite of the pentasil type. In another embodiment of the invention, the catalyst is a zeolite of the Y type.

The catalyst used has a specific crystallinity. It is preferable for the catalysts to have>70% crystallinity. It is particularly preferable for the crystallinity of the catalysts to be over 95%.

The Si/Al ratio in the catalyst used is 7 to 200. The Si:Al ratio of the catalyst is adjusted by dealumination. It is preferable to conduct dealumination with steam. In another embodiment of the invention, dealumination is conducted with $SiCl_4$. In yet another embodiment of the invention, dealumination is conducted with mineral acid. Dealumination can also be conducted with organic complexing agents, e.g., EDTA. Dealumination can also be conducted with hexafluorosilicates.

It is preferable to conduct dealumination with a single or multiple steam treatment.

It is preferable to use the catalyst in the acid form. Preferably the acid form is prepared by ion exchange with Bronsted acids. The acid form can also be prepared by ion exchange with ammonium chloride.

Preferably the catalyst contains less than 0.2% $Na_2O$. Particularly preferably, the catalyst contains less than 0.05% $Na_2O$.

It is preferable for the catalyst to be made into an industrially usable form by extrusion or granulation with silica or alumina. The catalyst is preferably extruded in a zeolite:alumina ratio of 80:20. The extrudates are preferably 4 to 20 mm long and 1.5 to 4 mm in diameter.

The catalyst preferably has a life of at least 200 hours. Particularly preferably, the life is at least 400 hours.

The coking rate of the catalyst is less than 1% in 200 hours and less than 1.5% in 400 hours.

The unreacted educts are separated from the tert-butylamine formed. It is preferable for separation to take place by distillation.

In the distillation, ammonia and isobutene are drawn off as an azeotrope. Distillation preferably takes place at a pressure of 1 to 30 bars, but more preferably at 30 bars.

Distillation is preferably conducted in a main column with less than 60 plates. It is particularly preferable for the main column to have 10 to 30 plates. Preferably the main column has a reflux ratio of 0.5 to 10 and particularly preferably, 0.6 to 3.

The process is preferably conducted by compressing recirculating ammonia and isobutene in the liquid state to the pressure of the reaction.

Preferably, the liquids are heated to the required reaction temperature.

Preferably, a small partial stream is tapped off and purified of inert components (e.g. isobutane) before being fed back into the process.

The invention will be explained in greater detail with the aid of the examples below.

Examples 1 to 16:

Three different types of catalyst are prepared for these examples.

Catalyst A

A Y zeolite is produced by traditional methods of synthesis and washed with acid. After extrusion with 20% alumina, ion exchange is completed by two treatments with $NH_4Cl$ at 80° C. It is then dried and calcined at 500° C. for 2 hours. The characteristic catalyst data are:

Si:Al ratio: 13.4

Crystallinity: >95%

$Na_2O$ content: <0.2%

Catalyst B

An HZSM-5 zeolite is produced according to traditional methods of synthesis and washed with acid. After extrusion with 20% alumina, ion exchange is completed by two treatments with $NH_4Cl$ at 80° C. It is then dried and calcined for 2 hours at 500° C. The characteristic catalyst data are:

Si:Al ratio: >150

Crystallinity: >95%

$Na_2O$ content: <0.2%

Ion exchange with copper is then performed in the conventional manner if required. In Examples 8 to 10, a ZSM-5 zeolite to which copper has been added is used, and in Examples 11 to 13 a ZSM zeolite in the H form is used.

Catalyst C

A zeolite is made by classical methods of synthesis and washed with acid. After extrusion with 20% alumina, ion exchange is completed by two treatments with $NH_4Cl$ at 80° C. It is then dried and calcined at 500° C. for 2 hours. The characteristic catalyst data are:

Si:A ratio: 397

Crystallinity: >95%

$Na_2O$ content: <0.2%

Reaction

All reactions are conducted in a tubular reactor according to FIG. 1 (material Inconel 600, volume 200 ml, inside diameter 2 cm). The educts are mixed in a similar mixing chamber packed with wire coils, and the product is separated from the unreacted educts in a distillation column packed with Raschig rings. The throughput is approximately 6 to 10 mol/(kg cat.h).

TABLE 1

| Example | Temperature (°C.) | Pressure | Catalyst | Molar Ratio $NH_3$: Isobutene | Conversion % |
|---|---|---|---|---|---|
| 1 | 300 | 100 | A | 2:1 | 6.4 |
| 2 | 300 | 100 | A | 4:1 | 6.5 |
| 3 | 250 | 100 | A | 2:1 | 2.2 |
| 4 | 280 | 100 | A | 2:1 | 5.5 |
| 5 | 300 | 100 | C | 2:1 | 6.3 |
| 6 | 300 | 100 | C | 1:1 | 5.6 |
| 7 | 300 | 100 | C | 0.9:1 | 5.4 |
| 8 | 300 | 100 | B | 2:1 | 7.1 |
| 9 | 280 | 100 | B | 2:1 | 6.5 |
| 10 | 280 | 100 | B | 1:1 | 6.4 |
| 11 | 300 | 150 | B | 2:1 | 9.5 |
| 12 | 300 | 200 | B | 2:1 | 10.2 |
| 13 | 300 | 250 | B | 2:1 | 11.6 |
| 14 | 300 | 100 | C | 0.3:1 | 3.3 |
| 15 | 300 | 100 | C | 0.5:1 | 2.2 |
| 16 | 300 | 100 | C | 0.3:1 | 1.8 |

Examples 17 to 22:
Catalyst B is used for Examples 17 to 22.
Table 2 reproduces the results of this experiment.

TABLE 2

| Example | Temperature | Pressure (bars) | TBA Yield (wt. %) | By-products (Fl. %, by GC) |
|---|---|---|---|---|
| 17 | 250 | 100 | 3.15 | none detected |
| 18 | 280 | 100 | 6.95 | none detected |
| 19 | 300 | 100 | 6.6 | none detected |
| 20 | 300 | 150 | 7.75 | none detected |
| 21 | 300 | 200 | 11.95 | 0.8 to 1.5 |
| 22 | 350 | 200 | 7.23 | 0.6 to 3.5 |

The $NH_3$: isobutene molar ratios are between 1.8 and 2.2:1.

With all experiments conducted at a temperature of 300° C. and a pressure of less than 200 bars, selectivity is independent of the ammonia:isobutene molar ratio and amounts to 100% by the above-defined gas chromatography method.

Example 23:

The reactor according to the drawing (FIG. 1; experimental setup) is filled with 70 g of catalyst A. The distillation column is filled with glass Raschig rings. After flushing twice with $N_2$, the reactor is heated to 300° C. and flushed for 15 minutes with $NH_3$. Then the reaction pressure is adjusted to 150 bar by an appropriate addition of $NH_3$. The reaction is started by adding 99.5% pure technical isobutene. The molar ratio is adjusted to 2:1 ammonia:isobutene by metering the two educts. The product stream is guided into the distillation column and freed of the unreacted educts with a reflux ratio of 0.8. The tert-butylamine formed (>99.7 wt. % pure) is drawn off from the bottom. The azeotropic mixture of isobutene and ammonia removed is drawn from the column as a liquid phase. After operating for 220 hours the reactor is shut down and the catalyst analyzed.

The color of the catalyst is white, as it is at the beginning of the experiment; the coke content is found to be 0.4% by TGA. The selectivity of the formation of the tert-butylamine is >99.85 wt. % as soon as steady-state conditions are reached.

Figure 2:
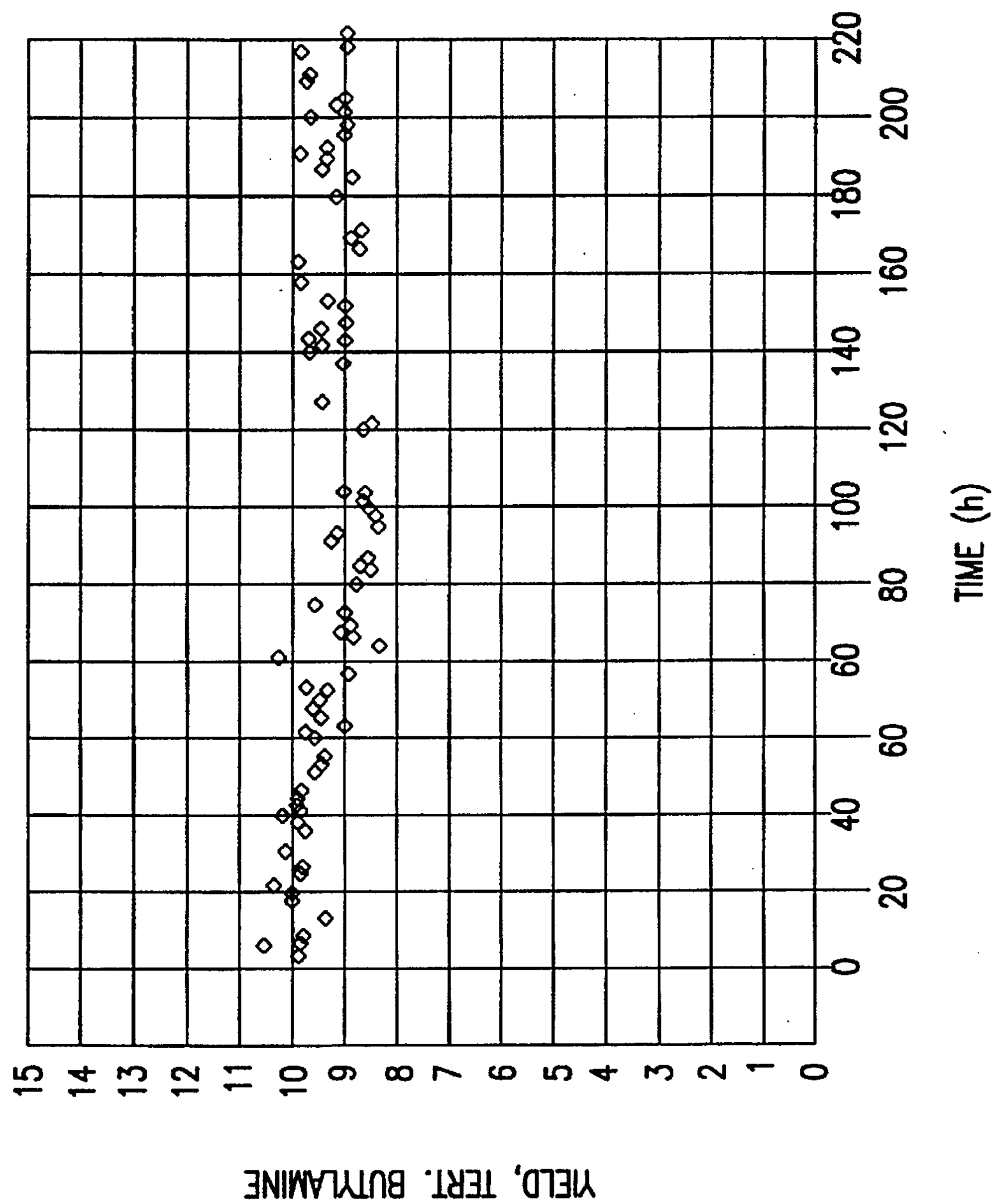
FIG. 2 is a graph of tert-butylamine yield over time from Example 23.

The reaction is maintained at a constantly high level throughout the entire test, as indicated by FIG. 2.

What we claim is:

1. A process for the production of tertiary butylamine having a purity of at least 99.5% and being suited for use without further purification, the process comprising reacting isobutene and ammonia in the gaseous phase above a dealuminized silica alumina catalyst, wherein the catalyst:

a) is used in acid form;

b) has a crystallinity of at least 95%;

c) has an $Na_2O$ content less than 0.2% by weight; and d) has a ratio of Si:Al greater than 12, and wherein the reaction occurs at a temperature of 200°–350° C., a pressure of 100–250 bar, and has a ratio of educt to catalyst of 5 to 60 moles/kg catalyst per hour.

2. A process according to claim 1, wherein the isobutene is an industrial isobutene having a purity less than 99.5%.

3. A process according to claim 1, wherein the isobutene is pure isobutene having a purity greater than 99.9%.

4. A process according to claim 1, wherein the ratio of educt to catalyst is 10 to 30 moles/kg catalyst per hour.

5. A process according to claim 1, wherein said ammonia and isobutene are present in a molar ratio of 0.9:1 to 4:1 ammonia to isobutene.

6. A process according to claim 1, wherein the Si:Al ratio of the catalyst is greater than 12 and less than 400.

7. A process according to claim 1, wherein the $Na_2O$ content of the catalyst is less than 0.05%.

8. A process according to claim 1, further comprising the step of separating non-converted educts of isobutene and ammonia from the tertiary butylamine.

9. A process according to claim 8, wherein separation of the non-converted educts is by distillation.

10. A process according to claim 9 wherein the ammonia and isobutene are distilled as azeotropes.

11. A process according to claim 9, wherein the distillation is at a pressure of 1–30 bar.

12. A process according to claim 1, further comprising a step of recycling non-converted products, wherein the non-converted products are in liquid form.

13. A process according to claim 12, further comprising the steps of compressing the recycled non-converted products in the liquid state to the reaction pressure, and heating the recycled non-converted products to the reaction temperature.

14. A process according to claim 12, further comprising the steps of withdrawing a small partial stream, purifying the small partial stream to remove inert parts and recycling the stream into the process.

15. A process according to claim 1, further comprising starting a reactor by the steps of:

a) rinsing a reactor several times with $N_2$, thereby removing air;

b) heating the reactor to an operating temperature;

c) rinsing the reactor with ammonia;

d) adjusting an operating pressure of the reactor in an ammonia atmosphere;

e) introducing to the reactor a quantity of isobutene sufficient to obtain a desired molar ratio in a reaction mixture;

f) obtaining a stationary reaction equilibrium; and g) adding to the stationary reaction equilibrium educts in a desired molar ratio while continuously withdrawing the reaction mixture.

* * * * *

UNITED STATES PATENT AND TRADEMARK OFFICE
CERTIFICATE OF CORRECTION

PATENT NO. : 5,648,546

DATED : July 15, 1997

INVENTOR(S) : Manfred BERGFELD and Martin NYWIT

It is certified that error appears in the above-indentified patent and that said Letters Patent is hereby corrected as shown below:

On the front cover:

[73] Assignee: AKZO NOBEL N.V., Velperweg, The Netherlands

Column 1, line 4, change "application" to --Application--.
Column 3, line 21, both occurrences, change "cat.h" to --cat·h--;
line 22, change "cat.h" to --cat·h--; and
line 63, change "Bronsted" to --Brönsted--.
Column 4, line 62, change "Si:A" to --Si:Al--.
Column 5, line 5, change "cat.h" to --cat·h--.

Signed and Sealed this

Twenty-fifth Day of November, 1997

Attest:

BRUCE LEHMAN

Attesting Officer

*Commissioner of Patents and Trademarks*